(12) United States Patent
Cincotta

(10) Patent No.: US 11,878,974 B2
(45) Date of Patent: Jan. 23, 2024

(54) COMPOSITION AND METHOD FOR TREATING METABOLIC DISORDERS

(71) Applicant: VeroScience LLC, Tiverton, RI (US)

(72) Inventor: Anthony H. Cincotta, Tiverton, RI (US)

(73) Assignee: VeroScience LLC, Tiverton, RI (US)

( * ) Notice: Subject to any disclaimer, the term of this patent is extended or adjusted under 35 U.S.C. 154(b) by 381 days.

(21) Appl. No.: 17/149,017

(22) Filed: Jan. 14, 2021

(65) Prior Publication Data

US 2021/0130344 A1 May 6, 2021

Related U.S. Application Data

(60) Continuation of application No. 17/117,999, filed on Dec. 10, 2020, now Pat. No. 11,560,375, which is a
(Continued)

(51) Int. Cl.
*A61K 31/48* (2006.01)
*C07D 457/06* (2006.01)
(Continued)

(52) U.S. Cl.
CPC ............ *C07D 457/06* (2013.01); *A61K 31/48* (2013.01); *A61K 31/4985* (2013.01); *C07C 59/265* (2013.01); *C07D 498/14* (2013.01)

(58) Field of Classification Search
CPC .......................... A61K 31/48; A61K 31/4985
See application file for complete search history.

(56) References Cited

U.S. PATENT DOCUMENTS 941,005 A 11/1909 Brandt
3,752,814 A 8/1973 Fluckiger
(Continued)

FOREIGN PATENT DOCUMENTS

CA 2166204 4/2009
CN 102283844 6/2014
(Continued)

OTHER PUBLICATIONS

Gould, International Journal of Pharmaceutics, 33(1986) 201-217 (Year: 1986).*
(Continued)

*Primary Examiner* — San Ming R Hui
(74) *Attorney, Agent, or Firm* — Fish & Richardson P.C.

(57) ABSTRACT

Bromocriptine citrate administered to a vertebrate, animal or human, can be used for any purpose including, e.g., the long-term modification and regulation of metabolic disorders, including prediabetes, obesity, insulin resistance, hyperinsulinemia, hyperglycemia and type 2 diabetes mellitus (T2DM) and/or, e.g., the treatment of other medical disorder(s) including immune or endocrine disorders or diseases. Bromocriptine citrate is administered over a limited or extended period at a time of day dependent on re-establishing the normal circadian rhythm of central dopaminergic activity of healthy members of a similar species and sex. Insulin resistance, hyperinsulinemia and hyperglycemia, T2DM, prediabetes, MS or all, can be controlled in humans on a long term basis by such treatment inasmuch as the daily administration of bromocriptine citrate resets neuronal activity timing in the neural centers of the brain to produce long term effects.

31 Claims, 1 Drawing Sheet

Related U.S. Application Data continuation of application No. 15/796,362, filed on Oct. 27, 2017, now Pat. No. 10,894,791, which is a division of application No. 15/492,891, filed on Apr. 20, 2017, now abandoned.

(60) Provisional application No. 62/325,342, filed on Apr. 20, 2016.

(51) Int. Cl.
*A61K 31/4985* (2006.01)
*C07D 498/14* (2006.01)
*C07C 59/265* (2006.01)

(56) References Cited

U.S. PATENT DOCUMENTS

| | | |
|---|---|---|
| 4,654,345 A | 3/1987 | Cavanak |
| 4,659,715 A | 4/1987 | Meier et al. |
| 4,749,709 A | 6/1988 | Meier et al. |
| 4,783,469 A | 11/1988 | Meier et al. |
| 5,006,526 A | 4/1991 | Meier et al. |
| 5,066,495 A | 11/1991 | Moro et al. |
| 5,186,420 A | 2/1993 | Beauchamp et al. |
| 5,344,832 A | 9/1994 | Cincotta et al. |
| 5,468,755 A | 11/1995 | Cincotta et al. |
| 5,496,803 A | 3/1996 | Meier et al. |
| 5,523,082 A | 6/1996 | Corbiere |
| 5,554,623 A | 9/1996 | Cincotta et al. |
| 5,565,454 A | 10/1996 | Cincotta |
| 5,585,347 A | 12/1996 | Cincotta et al. |
| 5,626,860 A | 5/1997 | Cincotta et al. |
| 5,635,512 A | 6/1997 | Cincotta et al. |
| 5,654,313 A | 8/1997 | Cincotta et al. |
| 5,668,155 A | 9/1997 | Cincotta et al. |
| 5,679,685 A | 10/1997 | Cincotta et al. |
| 5,688,794 A | 11/1997 | Cincotta et al. |
| 5,696,128 A | 12/1997 | Cincotta et al. |
| 5,700,795 A | 12/1997 | Cincotta et al. |
| 5,700,800 A | 12/1997 | Cincotta et al. |
| 5,712,265 A | 1/1998 | Cincotta et al. |
| 5,714,519 A | 2/1998 | Cincotta et al. |
| 5,716,932 A | 2/1998 | Meier et al. |
| 5,716,933 A | 2/1998 | Meier et al. |
| 5,716,957 A | 2/1998 | Cincotta et al. |
| 5,716,962 A | 2/1998 | Cincotta et al. |
| 5,719,160 A | 2/1998 | Cincotta et al. |
| 5,731,287 A | 3/1998 | Meier et al. |
| 5,731,312 A | 3/1998 | Cincotta et al. |
| 5,741,503 A | 4/1998 | Cincotta et al. |
| 5,744,477 A | 4/1998 | Cincotta et al. |
| 5,750,519 A | 5/1998 | Cincotta et al. |
| 5,756,513 A | 5/1998 | Cincotta et al. |
| 5,760,047 A | 6/1998 | Cincotta et al. |
| 5,792,748 A | 8/1998 | Cincotta et al. |
| 5,814,638 A | 9/1998 | Lee et al. |
| 5,830,895 A | 11/1998 | Cincotta et al. |
| 5,854,255 A | 12/1998 | Cincotta et al. |
| 5,866,584 A | 2/1999 | Cincotta et al. |
| 5,872,127 A | 2/1999 | Cincotta et al. |
| 5,872,133 A | 2/1999 | Cincotta et al. |
| 5,877,183 A | 3/1999 | Cincotta |
| 5,902,811 A | 5/1999 | Cincotta |
| 5,905,083 A | 5/1999 | Cincotta et al. |
| 5,952,329 A | 9/1999 | Cincotta et al. |
| 6,004,972 A | 12/1999 | Cincotta et al. |
| 6,071,914 A | 6/2000 | Cincotta et al. |
| 6,075,020 A | 6/2000 | Cincotta et al. |
| 6,855,707 B2 | 2/2005 | Cincotta |
| 7,888,310 B2 | 2/2011 | Cincotta |
| 8,021,681 B2 | 9/2011 | Cincotta |
| 8,137,992 B2 | 3/2012 | Cincotta |
| 8,137,993 B2 | 3/2012 | Cincotta |
| 8,137,994 B2 | 3/2012 | Cincotta |
| 8,431,155 B1 | 4/2013 | Cincotta et al. |
| 8,613,947 B2 | 12/2013 | Cincotta et al. |
| 8,741,918 B2 | 6/2014 | Cincotta |
| 8,821,915 B2 | 9/2014 | Cincotta |
| 8,877,708 B2 | 11/2014 | Cincotta |
| 9,192,576 B2 | 11/2015 | Cincotta et al. |
| 9,205,084 B2 | 12/2015 | Cincotta |
| 9,352,025 B2 | 5/2016 | Cincotta |
| 9,364,515 B2 | 6/2016 | Cincotta |
| 9,415,005 B2 | 8/2016 | Cincotta |
| 9,522,117 B2 | 12/2016 | Cincotta et al. |
| 9,655,865 B2 | 5/2017 | Cincotta |
| 9,700,555 B2 | 7/2017 | Cincotta et al. |
| 9,895,422 B2 | 2/2018 | Cincotta |
| 9,925,186 B2 | 3/2018 | Cincotta |
| 9,993,474 B2 | 6/2018 | Cincotta et al. |
| 9,999,653 B2 | 6/2018 | Cincotta |
| 10,137,132 B2 | 11/2018 | Cincotta |
| 10,238,653 B2 | 3/2019 | Cincotta |
| 10,307,421 B2 | 6/2019 | Cincotta et al. |
| 10,675,282 B2 | 6/2020 | Cincotta |
| 10,688,094 B2 | 6/2020 | Cincotta et al. |
| 10,688,155 B2 | 6/2020 | Cincotta |
| 10,894,791 B2 | 1/2021 | Cincotta |
| 11,000,522 B2 | 5/2021 | Cincotta et al. |
| 11,045,464 B2 | 6/2021 | Cincotta |
| 11,241,429 B2 | 2/2022 | Cincotta |
| 11,510,921 B2 | 11/2022 | Cincotta |
| 11,560,375 B2 | 1/2023 | Cincotta |
| 11,607,455 B2 | 3/2023 | Cincotta |
| 2001/0016582 A1 | 8/2001 | Cincotta |
| 2002/0146400 A1 | 10/2002 | Cincotta |
| 2002/0187985 A1 | 12/2002 | Cincotta |
| 2004/0028613 A1 | 2/2004 | Quay |
| 2004/0077679 A1 | 4/2004 | Cincotta |
| 2004/0081678 A1 | 4/2004 | Cincotta |
| 2004/0102383 A1 | 5/2004 | Cincotta et al. |
| 2004/0220190 A1 | 11/2004 | Cincotta |
| 2005/0054652 A1 | 3/2005 | Cincotta |
| 2005/0054734 A1 | 3/2005 | Cincotta |
| 2005/0079203 A1 | 4/2005 | Cincotta |
| 2005/0215558 A1 | 9/2005 | Cincotta |
| 2007/0004617 A1 | 1/2007 | Tsai |
| 2008/0200453 A1 | 8/2008 | Cincotta |
| 2008/0293735 A1 | 11/2008 | Cincotta |
| 2009/0137598 A1 | 5/2009 | Cincotta |
| 2009/0137599 A1 | 5/2009 | Cincotta |
| 2009/0143390 A1 | 6/2009 | Cincotta |
| 2010/0035886 A1 | 2/2010 | Cincotta et al. |
| 2011/0136817 A1 | 6/2011 | Cincotta |
| 2011/0195970 A1 | 8/2011 | Cincotta |
| 2011/0195971 A1 | 8/2011 | Cincotta |
| 2012/0129783 A1 | 5/2012 | Cincotta |
| 2012/0142582 A1 | 6/2012 | Cincotta |
| 2013/0197005 A1 | 8/2013 | Cincotta |
| 2013/0274246 A1 | 10/2013 | Cincotta |
| 2013/0287848 A1 | 10/2013 | Cincotta et al. |
| 2014/0031359 A1 | 1/2014 | Cincotta |
| 2014/0051685 A1 | 2/2014 | Cincotta |
| 2014/0187560 A1 | 7/2014 | Cincotta et al. |
| 2014/0249136 A1 | 9/2014 | Cincotta |
| 2014/0342975 A1 | 11/2014 | Cincotta |
| 2015/0011554 A1 | 1/2015 | Cincotta et al. |
| 2015/0024995 A1 | 1/2015 | Cincotta |
| 2015/0335641 A1 | 11/2015 | Cincotta |
| 2016/0032488 A1 | 2/2016 | Takahashi et al. |
| 2016/0038424 A1 | 2/2016 | Cincotta et al. |
| 2016/0263181 A1 | 9/2016 | Cincotta |
| 2016/0271222 A1 | 9/2016 | Cincotta |
| 2016/0324848 A1 | 11/2016 | Cincotta |
| 2017/0020871 A1 | 1/2017 | Cincotta et al. |
| 2017/0209539 A1 | 7/2017 | Cincotta |
| 2017/0305898 A1 | 10/2017 | Cincotta |
| 2017/0340271 A1 | 11/2017 | Cincotta |
| 2017/0340632 A1 | 11/2017 | Cincotta et al. |
| 2018/0051019 A1 | 2/2018 | Cincotta |
| 2018/0125843 A1 | 5/2018 | Cincotta |
| 2018/0140675 A1 | 5/2018 | Cincotta |
| 2018/0177874 A1 | 6/2018 | Cincotta |
| 2018/0263978 A1 | 9/2018 | Cincotta et al. |

(56) References Cited

U.S. PATENT DOCUMENTS

| | | |
|---|---|---|
| 2019/0160059 A1 | 5/2019 | Cincotta et al. |
| 2019/0167677 A1 | 6/2019 | Cincotta |
| 2019/0343833 A1 | 11/2019 | Cincotta et al. |
| 2020/0253970 A1 | 8/2020 | Cincotta |
| 2020/0276193 A1 | 9/2020 | Cincotta et al. |
| 2021/0085787 A1 | 3/2021 | Cincotta |
| 2021/0094946 A1 | 4/2021 | Cincotta |
| 2021/0177839 A1 | 6/2021 | Cincotta |
| 2021/0228576 A1 | 7/2021 | Cincotta et al. |
| 2021/0401824 A1 | 12/2021 | Cincotta |
| 2022/0125379 A1 | 4/2022 | Cincotta |
| 2022/0142960 A1 | 5/2022 | Cincotta et al. |
| 2022/0265648 A1 | 8/2022 | Cincotta |
| 2022/0288209 A1 | 9/2022 | Cincotta |
| 2023/0150999 A1 | 5/2023 | Cincotta |

FOREIGN PATENT DOCUMENTS

| | | | |
|---|---|---|---|
| CN | 102727894 | | 10/2015 |
| GB | 2192541 | * | 1/1988 |
| JP | H02-121919 | | 5/1990 |
| WO | WO 2002/083141 | | 10/2002 |
| WO | WO 2009/091576 | | 7/2009 |
| WO | WO 2013/165902 | | 11/2013 |
| WO | WO 2017/184875 | | 10/2017 |

OTHER PUBLICATIONS

Berge et al., Journal of Pharmaceutical Sciences, 66, 1 1977, 1-19.
Dietrich et al., Best Practice & Research Clinical Gastroenterology, 2014:28;637-653 (Year: 2014).
Dosage Forms: Non-Parenteral in Encyclopedia of Pharmaceutical Technology, Singh et al., 2008, 749-761.
Pan, "Industrial Pharmaceutics," China Medical Science and Technology Press, the first printing of the 3rd edition, Aug. 2015, p. 47 (Partial English Translation only).
PCT International Search Report and Written Opinion in Application No. PCT/US2017/028656, dated Jul. 7, 2017.
Pharmaceutical Salts: Properties, Selection, and Use, P. Stahl and Camille Wermuth, Eds. 2002, 329- 345.
Pukngam et al., "Development and Validation of a Stability-Indicating HPLC Method for Determination of Bromocriptine Mesylate in Bulk Drug and Tablets," Current Pharmaceutical Analysis, 2013, 9:92-101.
Rowe et al., Stearic Acid, Handbook of Pharmaceutical Excipients, 6th ed, 2009, 697-699.
Rowe et al., Mannitol, Handbook of Pharmaceutical Excipients, 7th ed, 2012, 479-482.
Vicchi et al., "Dopaminergic drugs in type 2 diabetes and glucose homeostasis," 93735Pharmacological Research, Dec. 2015, 109: 74-80.
An English translation of each document (or of the pertinent portions thereof), or each corresponding English-language patent or application, or English-language abstract (or claim) is enclosed.
[No Author Listed], "Dissolution," General Chapter 711, U.S. Pharmacopoeia (USP), 34th ed., Dec. 1, 2011, 8 pages.
EP Extended European Search Report in European Appln No. 18868516.8, dated Jun. 29, 2021, 8 pages.
PCT International Preliminary Report on Patentability in International Appln PCT/US2018/056554, dated Apr. 21, 2020, 15 pages.
PCT International Search Report and Written Opinion in International Appl. PCT/US2018/056554, dated Jan. 3, 2019, 17 pages.
Rathbone et al., academia.edu [Online], "Modified-Release Drug Delivery Technology," Marcel Dekker, Inc., 2003, [Retrieved on Nov. 23, 2018], retrieved from: URL<https:www.academia.edu/28583222/Modified-Release_Drug_Delivery_Technology?auto=downloade>, 90 pages.
Pursuant to 37 C.F.R. § 1.98(a)(2)(ii), the U.S. Patent(s) and/or U.S. Patent Application Publication(s) on PTO/SB/08 is/are not being submitted.

* cited by examiner

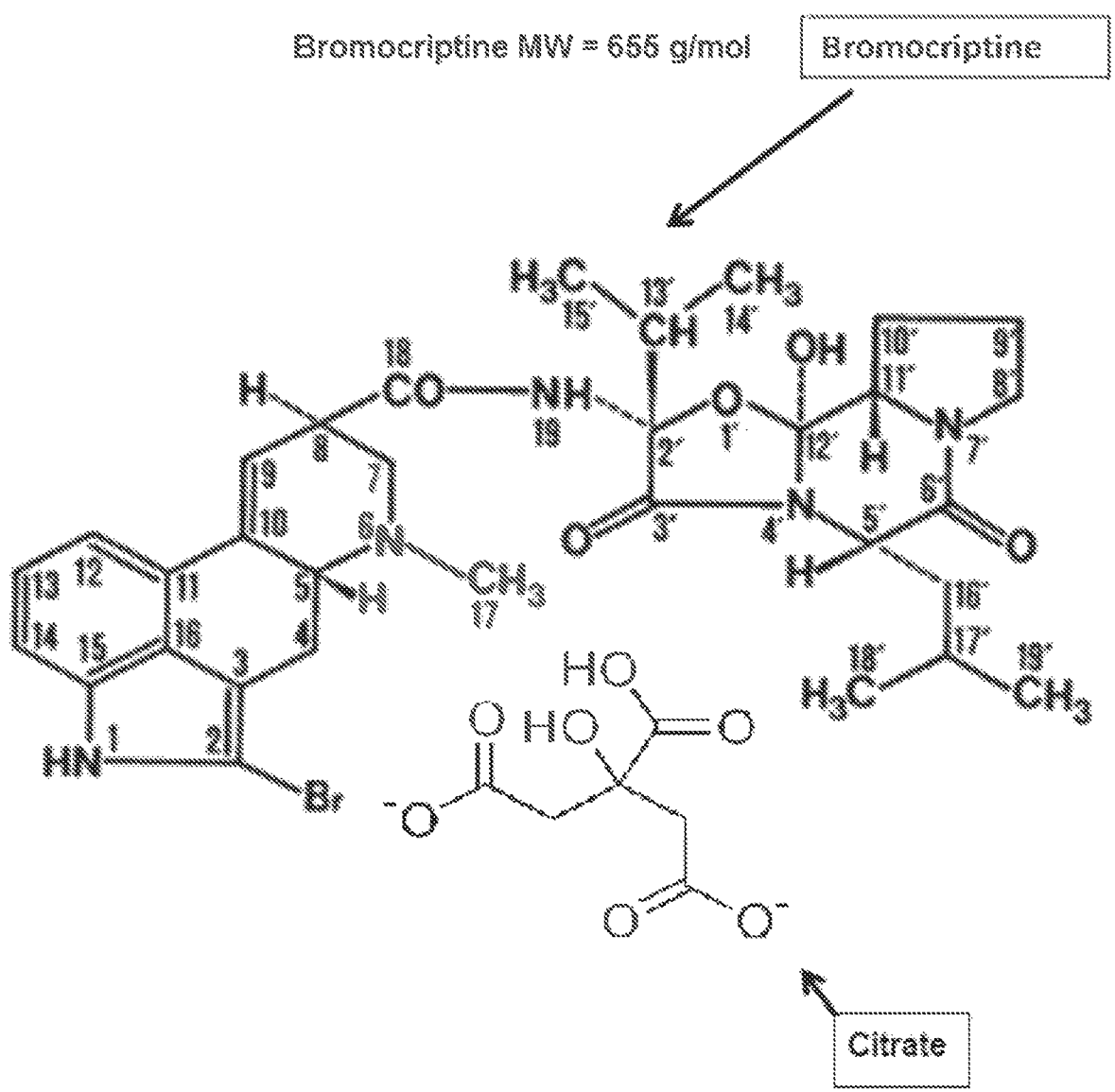

COMPOSITION AND METHOD FOR TREATING METABOLIC DISORDERS

FIELD OF THE INVENTION

The present invention relates to synthesis of bromocriptine citrate, and to compositions and dosage forms containing bromocriptine citrate that provide increased stability and water solubility compared to prior art bromocriptine dosage forms. In another aspect, the invention relates to methods for using these compositions and dosage forms for the treatment of metabolic disorders including type 2 diabetes mellitus (T2DM).

BACKGROUND OF THE INVENTION

Diabetes, one of the most insidious of the major diseases, can strike suddenly or lie undiagnosed for years while attacking the blood vessels and nerves. Diabetics, as group, are far more often afflicted with blindness, heart disease, stroke, kidney disease, hearing loss, gangrene and impotence. The total costs of diagnosed diabetes were estimated by the American Diabetes Association to be $245 billion in 2012 alone, an increase of over 40% over a five-year period (compared to 2007) and a figure that represents about 20% of all health care spending in the United States.

Diabetes adversely affects the way the body uses sugars and starches which, during digestion, are converted into glucose. Insulin, a hormone produced by the pancreas makes the glucose available to the body's cells for energy. Insulin is a hormone with a multitude of biological activities, many of which are tissue specific. For example, insulin can augment milk production in the mammary gland, stimulate fat synthesis in the liver, promote the transport of glucose into muscle tissue, stimulate growth of connective tissues, and the like. The effects of the insulin molecule in one tissue are not necessarily dependent upon its effect in other tissues. That is, these insulin activities can be and are molecularly separate from each other. In muscle, adipose (fat) and connective tissues, insulin facilitates the entry of glucose into the cells by an action on the cell membranes. The ingested glucose is normally metabolized in the liver to $CO_2$ and $H_2$ (50%), glycogen (5%) and fat (30-40%), which is stored in fat depots. Fatty acids are circulated, returned to the liver and metabolized to ketone bodies for utilization as a source of energy by various tissues. Fatty acids are also metabolized by other organs, fat formation being a major pathway for carbohydrate utilization. The net effect of insulin is to promote the storage and use of carbohydrates, protein and fat. Insulin deficiency is a common and serious pathological condition in man.

In type 1 diabetes, the pancreas produces little or no insulin, and insulin must be injected daily for the survival of the diabetic. In type 2 diabetes (T2DM), the pancreas produces insulin, but the amount of insulin is insufficient, or less than fully effective due to cellular resistance, or both. In both type 1 and type 2 diabetes, the fundamental defects to which the abnormalities can be traced are: (1) a reduced entry of glucose into various "peripheral" tissues, and (2) an increased liberation of glucose into the circulation from the liver (increased hepatic glucogenesis). There is therefore an extracellular glucose excess and an intracellular glucose deficiency which has been called "starvation in the midst of plenty." There is also a decrease in the entry of amino acids into muscle and an increase in lipolysis. These result, as a consequence of the diabetic condition, in elevated levels of glucose in the blood, and prolonged high blood sugar which is indicative of a condition which will cause blood vessel and nerve damage. Obesity, or excess fat deposits, is often associated with increasing cellular resistance to insulin which precedes the onset of frank diabetes. Prior to the onset of diabetes, the pancreas of the obese are taxed to produce additional insulin, but eventually, perhaps over several years, insulin productivity falls and diabetes results.

Obesity and insulin resistance, the latter of which is generally accompanied by hyperinsulinemia or hyperglycemia, or both, are hallmarks of T2DM. Hyperinsulinemia is a higher-than-normal level of insulin in the blood. Insulin resistance can be defined as a state in which a normal amount of insulin produces a subnormal biologic response. In insulin-treated patients with diabetes, insulin resistance is considered to be present whenever the therapeutic dose of insulin exceeds the secretory rate of insulin in normal persons. Insulin resistance is also found in the setting defined by higher-than-normal levels of insulin—i.e., hyperinsulinemia—when normal or elevated levels of blood glucose are present. Despite decades of research on these serious health problems, the etiology of obesity and insulin resistance is unknown.

Metabolism is a complex orchestration of biochemical processes among cells and tissues of the body all working in concert to ensure the survival of the organism as a whole. The central nervous system plays a major role in integrating these metabolic activities to maintain normal biological homeostasis within the body. Environmental and genetic perturbations to this central nervous system control of metabolism can manifest as a range of metabolic disorders. Additionally, since metabolic processes have profound effects on the entire body, diseases and disorders affecting metabolism generally affect other areas of the body as well. For example, individuals suffering from T2DM often experience problems with several body organs and systems. Typically, plasma glucose levels are elevated in T2DM as a result of the body's resistance to the glucose-lowering effects of insulin as well as a decreased ability to secrete appropriate amounts of insulin after a meal. T2DM is associated with damage to various organs such as the eyes, nerves, and kidneys. The disease is also associated with substantially increased risk for cardiovascular disease (CVD), the leading cause of death in type 2 diabetics.

Multiple circadian central neural oscillations govern the regulation and coordination of multiple physiological (e.g., metabolic) events in the periphery as a function of their circadian phase relationship, described in U.S. Pat. No. 5,468,755 and herein incorporated in entirety by reference. One such circadian rhythm governing metabolic status is the central (hypothalamic) circadian rhythm of dopaminergic activity. It has previously been observed that phase shifts in the circadian rhythm of central dopaminergic activities influence the status of metabolic diseases such as obesity or diabetes. Phase shifts away from the healthy normal circadian rhythm of central or hypothalamic dopaminergic activity by environment, diet, stress, genetics and/or other factors are, further, also operative in a much different and broader physiological regulatory system and potentiate and lead to the multiple complex metabolic pathologies of and associated with metabolic syndrome (MS—a syndrome defined as a composite of any three of hypertriglyceridemia [plasma triglycerides at >150 mg/dl], hypertension [blood pressure at >130/85], central obesity, hyperglycemia of fasting plasma glucose >110 mg/dl, or low plasma HDL cholesterol of < about 35 mg/dl and often to include the presence of insulin resistance, fatty liver, and systemic low grade inflammation) as described herein. The circadian peak of central dopaminergic activity is diminished in individuals with metabolic disease. The timed administration of bromocriptine citrate is intended to reestablish the normal circadian peak of central dopaminergic activity. Furthermore, resetting these aberrant central dopaminergic circadian rhythms back towards that of the healthy normal state results in simultaneous improvements in the multiple complex pathologies of and associated with MS as described herein. As described above, MS and its associated pathologies represent a different pathology from diabetes or obesity, the cause of which is unknown. However, subjects with MS have much greater risk of developing cardiovascular disease than subjects without the syndrome. Inasmuch as obesity and T2DM are not always associated with MS and vice versa, it is clear that this major health risk represents a separate and unique metabolic state with unique characteristics.

Adjusting the circadian rhythm of central dopaminergic activities by various means (including, e.g., the administration of central dopamine agonist(s)) may be employed to reduce the many pathologies of and associated with this syndrome, e.g., aberrant vascular tone, vascular health, endothelial function, glucose and lipid metabolism, immune system functions specifically influencing the vasculature, insulin action, and blood coaguability. That is, administration of dopamine agonists can act centrally to readjust towards "normal" those aberrant (circadian) neuroendocrine events controlling peripheral metabolism in subjects with metabolic disease. This same circadian dopaminergic resetting methodology may also be utilized to treat cardiometabolic risk, a cluster of physiological pathologies of common or discordant origin that converge to increase risk of cardiovascular disease. These risk factors include those of MS, but also inflammation, endothelial dysfunction, hypercholesterolemia, diabetes (including T2DM), prediabetes, obesity, smoking, gender, and age. Further, rather than just increasing dopaminergic activity with central dopamine agonists to improve MS, cardiometabolic risk and their associated pathologies, one may better influence these conditions by timing the administration of such dopamine agonists to coincide with the daily peak in central dopaminergic activities of healthy subjects of the same (or similar) species and sex to derive maximal benefit from such dopamine agonist therapy in treating these conditions. Central acting dopamine agonists are known in the art and include, but are not limited to, e.g., bromocriptine, quinpirole, quinerolane, talipexole, ropinirole, apomorphine, lisuride, terguride, fenoldopam, dihydroergotoxine (hydergine), erfotoxine, dihydroergocryptine, 6-methyl 8 β-carbobenzyloxy-aminoethyl-lO-α-ergoline, 8-acylaminoergoline, 6-methyl-8-α-(N-acyl)amino-9-ergoline, dihydro-alpha-ergocriptine, dihydro-alpha-ergotoxine, 6-methyl-8-α-(N-phenyl-acetyl) amino-9-ergoline, ergocornine, 9,10-dihydroergocornine, any D-2-halo-6-alkyl-8-substituted ergoline, D-2-bromo-6-methyl-8-cyanomethylergoline, and combinations thereof. Of these, bromocriptine, lisuride, or other ergot-related compounds with little or no serotonin $5HT_{2b}$ receptor agonist activity are most preferred.

Because of its unique central mechanism of action, dopamine agonist (e.g., bromocriptine) therapy may be effectively combined with various peripheral acting agents that target specific peripheral biochemistry operative in manifesting particular elements of metabolic disease that may not be fully alleviated by dopamine agonist therapy, e.g., HMG-CoA reductase inhibitors to reduce elevated plasma cholesterol, anti-hypertensives to reduce blood pressure by mechanisms different from those of dopamine agonist therapy, and anti-diabetes agents that augment the resetting effect of dopamine agonists on glucose metabolism such as postprandial insulin secretagouges or insulin itself, anti-inflammatory agents, and anti-coagulative agents. Examples of such agents are known in the art and are disclosed in, e.g., Int'l. Pat. App. Pub. No. WO 2009/091576 A2.

Use of such centrally acting dopamine agonists for treatment of the metabolic and non-metabolic vascular disorders described herein may be potentiated by their administration in a formulation that, upon administration, acts to re-establish the central nervous system circadian rhythm of dopaminergic activity as observed in healthy individuals of the same species and sex. One way to achieve this objective is to administer the bromocriptine citrate formulations disclosed herein within 2 hours after waking. Circadian rhythms of dopaminergic activity within the central nervous system, and particularly the phase relations of these dopaminergic neuronal rhythms with other circadian neuronal activities such as serotonergic neuronal activities have been demonstrated to regulate peripheral glucose and lipid metabolism in a manner dependent upon the phase of the daily peak in circadian central dopaminergic activity. Centrally acting dopamine agonists (e.g., bromocriptine) may be administered to effect a peak of dopamine agonist in the circulation that can be used to impact a circadian neuro-oscillator system (e.g., suprachiasmatic nucleus) in the brain to positively influence its regulation of metabolism via output control over other metabolism regulatory centers in the brain to thereby improve peripheral metabolism immediately followed by a brief (1-3 hours) sustained lower level of release of dopamine agonist into the circulation for a determined period of time that can directly influence other metabolism regulatory centers in the brain to improve metabolism.

Consequently, increases in dopaminergic activity at particular times of day versus others produce maximal effectiveness in improving metabolic diseases and disorders such as T2DM, obesity, prediabetes, metabolic syndrome, cardiometabolic risk, hypertension, dyslipidemia, insulin resistance, hyperinsulinemia, hepatic steatosis, renal disease, cardiovascular disease, cerebrovascular disease, and peripheral vascular disease and biomarkers of impending vascular disease. If (and only if) the dopamine agonist therapy is used at the appropriate dosage (0.05 µg to 0.5 mg/kg of body weight) and at the appropriate time of day (within 2 hours of awakening) so that its levels are not elevated throughout a greater portion of the day but are confined to a discrete daily interval of the day that approximates the natural daily circadian peak of central nervous system dopaminergic activity in healthy individuals without either metabolic disease, vascular disease or increased levels of metabolic or non-metabolic biomarkers of vascular disease and given to a subject in need of treatment for cardiovascular disease, then dopamine agonist therapy decreases the severity of metabolic disease, vascular disease and adverse vascular events.

As such, maximized successful treatment of these aforementioned pathologies and abnormalities may be accomplished by appropriately timed daily administration of centrally acting dopamine agonist(s) that result in the re-establishment of the natural central circadian rhythm of dopaminergic activity. Because such dopamine agonist therapy attacks a root cause of these metabolic disorders (central dysregulation of global peripheral metabolism) it is possible to effectuate improvements in several metabolic pathologies in a simultaneous fashion that is not generally achievable by other conventional means that attack particular specific symptoms of metabolic disease, e.g., hypertension, high cholesterol, and/or hyperglycemia, fatty liver, non-alcoholic steatotic hepatitis (NASH), by acting at specific downstream peripheral targets such as biochemical pathways within liver or muscle. Moreover, central dopamine agonist therapy may be coupled with direct or indirect peripheral acting therapeutic agents, e.g., anti-diabetes agents, antihypertensive agents, cholesterol lowering agents, anti-inflammatory agents, or anti-obesity agents to produce additive or synergistic improvements in metabolic disease such as obesity or T2DM or particular aspects of metabolic disease, e.g., hypertension associated with obesity or T2DM.

In accordance with this invention, the use of dopamine agonists, in particular the dopamine $D_2$ agonist bromocriptine ((5'α)-2-bromo-12'-hydroxy-2'-(1-methylethyl)-5'-(2-methylpropyl)-ergotaman-3',6',18-trione, CAS Registry No. 25614-03-3) or a salt formulation thereof, to treat the multiple complex pathologies of and associated with MS (including, e.g., obesity, insulin resistance, hyperlipidemia, hypertension, and hypertriglyceridemia), non-metabolic pathologies associated with MS (e.g., a pro-inflammatory state, a pro-coagulative state, pro-oxidant state, and/or endothelial dysfunction), arteriosclerosis, and/or cardiovascular disease, all in subjects with or without T2DM, is applied during specific daily intervals to maximize the effectiveness of such treatment. See e.g. published US patent application 2008-0293735 A1.

Bromocriptine is typically formulated as a mesylate salt (referred to as bromocriptine mesylate) in pharmaceutical preparations for the treatment of a variety of metabolic, reproductive, and endocrine disorders. Solid oral bromocriptine mesylate preparations are commercially available (e.g., CYCLOSET® tablets containing a total therapeutic dose of 0.8 mg bromocriptine mesylate or PARLODEL® tablets or capsules containing a total therapeutic dose of 2.5-5.0 mg bromocriptine mesylate). Mesylate salts are generally known in the art to confer more favorable interactions with water relative to other salts, including, e.g., the formic, esylate, bisulfate, citrate, napsylate, besylate, phosphate, tartrate, tosylate, oxalate, and hydrochloride salts.

However, the mesylate salt of bromocriptine nevertheless exhibits very poor (in absolute terms) water solubility and is additionally very susceptible to water degradation, two properties that significantly limit the optimization of the stability of bromocriptine formulations and their use in clinical medicine. As a result of the high susceptibility of the mesylate salt of bromocriptine to water degradation, the shelf life of the compound is limited in micro and macro environments that may contain water of any sort. Bromocriptine mesylate is further susceptible to heat degradation, particularly in aqueous/water environments. Additionally, as a direct result of the very poor water solubility of the mesylate salt of bromocriptine, this compound exhibits poor absorption across biological cellular membranes (e.g., epithelia). To compensate for these limitations of bromocriptine mesylate in an in vivo context (i.e., a warm, aqueous environment where drug effectiveness is reliant on absorption/diffusion across biological cellular membranes), higher dosages than would otherwise be necessary have been required.

SUMMARY OF THE INVENTION

The present disclosure provides bromocriptine citrate and compositions containing bromocriptine citrate, and methods of treatment of metabolic disorders using bromocriptine citrate and/or one or more compositions containing bromocriptine citrate.

More specifically, the present disclosure provides bromocriptine citrate. Bromocriptine citrate can be provided as a dosage form (e.g., a pharmaceutical dosage form) containing bromocriptine citrate and one or more pharmaceutically acceptable inert excipients.

The dosage form can be, e.g., an oral dosage form. The dosage form can include one or more low moisture content fillers, water-scavenging agents, and/or lubricants. The dosage form can include one or more excipients (e.g., a disintegrating agent) that affect the rate of bromocriptine citrate release from the dosage form. The dosage form can include cornstarch, mannitol, colloidal silicon dioxide, and/or stearic acid. The dosage form can include effective amounts of bromocriptine citrate for treating the metabolic disorders disclosed herein of between about 0.05 μg and about 0.5 mg/kg of body weight bromocriptine citrate and preferably between about 0.1 μg and about 0.3 mg/kg of body weight bromocriptine citrate and in an especially preferred embodiment between about 2 μg and 0.1 mg/kg of body weight bromocriptine citrate. The dosage form can include citric acid as an excipient. The dosage form can have a total weight (including excipients) of between about 2.5 mg and about 2000 mg.

Moreover, the present disclosure provides a method for therapeutically modifying and resetting the central circadian rhythm of dopaminergic activity of a vertebrate, to mimic that of a healthy individual of the same species and sex, the method including administering to the vertebrate bromocriptine citrate. The method can include orally and/or parenterally administering bromocriptine citrate to the vertebrate.

The present disclosure also features a method for treating metabolic disorders including T2DM in a subject in need of such treatment, the method including administering to the subject bromocriptine citrate. The method can include orally and/or parenterally administering bromocriptine citrate to the subject.

Another method featured by the present disclosure is a method for treating T2DM in a subject in need of such treatment, the method including administering to the subject an effective amount for treating T2DM of bromocriptine citrate. The method can include orally and/or parenterally administering bromocriptine citrate to the subject.

Any of the above-described methods can include the administration of any of the above-described dosage forms containing bromocriptine citrate. Any of the above-described methods can include the administration of between about 0.05 μg and about 0.5 mg/kg per day of bromocriptine citrate to the subject.

Any of the above-described methods can further include treating the subject with one or more additional therapeutic regimens. The additional therapeutic regimens can include, e.g., administering one or more dopamine D1 receptor agonists, alpha-1 adrenergic antagonists, alpha-2 adrenergic agonists, serotonergic inhibitors, and/or serotonin 5HT1b agonists. Alternately or in addition, the additional therapeutic regimens can include, e.g., administering one or more peripheral acting agents.

The period of a day is generally expressed in terms of 2400 hours. "BW" designates body weight, "kg" represents kilograms, "g" represents grams, "mg" represents milligrams, and "μg" represents micrograms. All parts and percentages are by weight unless explicitly stated otherwise. As used herein, except where otherwise indicated, the terms "about" and "approximately" are defined as being within plus or minus (±) 15%, preferably within ±10%, still more preferably within ±5% of the value as disclosed.

The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of metabolic disorders including T2DM).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 1 is a schematic showing a chemical representation of bromocriptine citrate.

DETAILED DESCRIPTION

After substantial experimentation with various dosage regimens, and contrary to the general teaching in the art that mesylate salts confer greater water solubility relative to other salts including citrate, it is surprisingly found that bromocriptine formulated as a citrate salt (referred to as bromocriptine citrate) has the unique ability to markedly improve the heat stability (i.e., protect against heat degradation), aqueous/water stability (i.e., protect against the aqueous/water degradation of bromocriptine) and aqueous/water solubility of bromocriptine compared to the mesylate salt of bromocriptine. As a result, compared to bromocriptine mesylate, bromocriptine citrate exhibits a better shelf life (storage stability) in pharmaceutical preparations and additionally provides for longer term stability profiles (i.e., longer duration of drug activity) in pharmaceutical preparations with respect to bromocriptine dissolution, allowing for a longer storage period between drug manufacture and drug administration, and/or less stringent (e.g., in terms of humidity or temperature) storage conditions. This feature allows for a more flexible (and, thus, less expensive) manufacturing process.

Bromocriptine citrate can be prepared directly from the bromocriptine free base or from the bromocriptine mesylate salt after desalting to the bromocriptine free base. Bromocriptine mesylate as well as the free base is commercially available from several sources (e.g., Sigma Aldrich and Euticals). Desalting of the bromocriptine mesylate to generate the bromocriptine free base can be accomplished by any of a variety of known desalting techniques. Such techniques are generally known in the art and include desalting by, e.g., gel filtration (e.g., Sephadex (cross-linked dextran gel) filtration column), dialysis, ion exchange column purification (effecting removal of mesylate by binding to the charged column), and/or diafiltration or ultrafiltration (use of permeable membranes to separate molecules based upon size). The solvent for the desalting process can be a variety of organic solvents and/or combinations of solvents, such as, e.g., methanol, ethanol, and/or chloroform. Also, the desalting process may additionally employ phase separation between aqueous and organic solvent phases, with the salt isolated in the aqueous phase and the bromocriptine isolated in the organic phase. Additionally, the free base of bromocriptine can be generated from the mesylate salt by extraction of the mesylate from bromocriptine by dissolving the bromocriptine mesylate in an organic solvent (not miscible with water) that forms a bilayer upon addition of an aqueous solution of a pH in which the mesylate migrates into the aqueous phase while the bromocriptine remains in the organic phase. The free base bromocriptine can subsequently be washed with repeated organic/aqueous separations and dried to purity.

Citric acid is a tribasic compound with pKa values of 3.13, 4.76, and 6.40. As such, the bromocriptine citrate described herein may be of the mono, di, or tri citrate forms or combinations thereof. Starting with the bromocriptine free base, the preparation of the citrate salt can be accomplished by any of the following general methods.

Method 1:

Citric acid (about 1-3 grams) is dissolved in absolute (i.e., about 100%) ethanol at room temperature in a reaction vessel, to which an ethanol solution of bromocriptine (about 2-10 grams) is then added in an equi-mole amount to the citric acid. Citric acid may also be present in excess of the bromocriptine free base. The resulting solution is stirred for about some time, e.g., 2-24 hours at room temperature and is then evaporated under vacuum, e.g., on a rotary evaporator. The resulting semi-solid or solid product is then dissolved in, e.g., an ethanol type mixture, e.g., straight ethanol or acetone-ethanol mixture (e.g., a 50:50 mixture) and subsequently dried under vacuum. Other mixtures (e.g., other organic solvent systems, e.g., methanol) and/or other mixture ratios (e.g., a 5:95, 10:90, 20:80, 25:75, 30:70, 40:60, 60:40, 70:30, 75:25, 80:20, 90:10, or 95:5 mixture) can be used. The resulting precipitate is bromocriptine citrate.

Method 2:

Citric acid (about 1-3 grams) is dissolved in methanol. Bromocriptine (about 2-10 grams) is also dissolved in methanol then added directly to the citrate citric acid solution in an equi-mole amount to the citric acid Citric acid may also be present in excess of the bromocriptine free base. The two solutions are then mixed and then stirred (about 2-24 hours at room temperature) and then evaporated to dryness (e.g., under vacuum, e.g., using a rotary evaporator). The resulting residue is bromocriptine citrate.

Method 3:

Citric acid (about 1-3 grams) is dissolved in butanol and bromocriptine (about 2-10 grams) dissolved in butanol is then added to this solution in an equi-mole amount to the citric acid (citric acid may also be present in excess of the bromocriptine free base) and stirred at room temperature for about 2-24 hours. The solvent is removed under vacuum; the resulting precipitate is bromocriptine citrate. The isolated precipitate may be re-dissolved in butanol and water to create a two phase system. The phases are separated and the organic phase is evaporated to dryness to yield purified bromocriptine citrate.

Method 4:

Citric acid (about 1-3 grams) is dissolved in a water/ethanol solvent, to which a water/ethanol solution containing bromocriptine (about 2-10 grams) is added in an equi-mole amount to the citric acid. Citric acid may also be present in excess of the bromocriptine free base. Various organic solution(s) containing bromocriptine can be used. For example, bromocriptine can be dissolved in one or more organic solvents, e.g., methanol, propanol, or butanol. The resulting solution is stirred at room temperature for about 2-24 hours; the solution is then evaporated to dryness. The dried solid can be washed in methanol and re-precipitated by evaporation to dryness. The resulting residue is bromocriptine citrate.

Method 5

Citric acid (about 1-3 grams) is dissolved in any organic solvent or aqueous/organic solvent in which bromocriptine is soluble. Bromocriptine (about 2-10 grams) is dissolved in the same organic solvent or aqueous/organic solvent as the citric acid or in a solvent that is miscible with the solvent used to solvate the citric acid and then added to and mixed with the citric acid/organic solution in an equi-mole amount to the citric acid. Citric acid may also be present in excess of the bromocriptine free base. The resulting solution is stirred at room temperature for about 2-24 hours. The solution is evaporated to dryness to yield bromocriptine citrate.

In each of the above examples it is preferred to use the citric acid and bromocriptine solutions at near their saturation point). One or more chemical modifications generally known in the art can be made to the above-described methods to enhance or optimize the purity and/or yield of bromocriptine citrate. For example, the pH of the bromocriptine and citric acid solutions may be adjusted to optimize the formation of the bromocriptine citrate. As further non-limiting examples, one or more organic solvents (e.g., methanol, propanol, or butanol) can be used to dissolve, re-suspend, and/or re-precipitate citric acid, bromocriptine, and/or bromocriptine citrate. The pKa of bromocriptine and citric acid can be adjusted, for example, by changing the solvent used to prepare the citric acid or bromorcriptine solutions. The basic forms of citric acid may also be employed in these methods (e.g. sodium citrate), though the citric acid form is preferred. One or more steps in any of the above-described methods can be carried out at a different (i.e., lower or higher) temperature or pH; alternately or in addition, the temperature can be varied over time during one or more steps. The final product (i.e., bromocriptine citrate) can be re-precipitated to reduce and/or remove any impurities (such as, e.g., bromocriptine free base or unassociated/unbound citric acid or water). In each method, the product can be "cleaned" (e.g., using one or more of the above-described techniques, e.g., dissolution, resuspension, and/or re-precipitation) to remove unreacted bromocriptine or citrate. Water may be removed by fractional distillation or other standard dewatering techniques known to those skilled in the art.

Further, bromocriptine citrate provides for pharmaceutical preparations with more efficient absorption across biological cellular membranes relative to bromocriptine mesylate. Still further, due to the unexpectedly improved degradation resistance of bromocriptine citrate to heat and water (e.g., in a physiological environment) and its simultaneously increased aqueous solubility (a phenomenon not predicted by the art) relative to bromocriptine mesylate, minimum and preferred dosages of bromocriptine citrate for treating vertebrates are lower than the minimum and preferred dosages of bromocriptine mesylate for an equivalent therapeutic effect and treatment duration. Taken together, the unanticipated advantages of bromocriptine citrate provide for a substantial improvement over the use of bromocriptine mesylate in current commercial bromocriptine pharmaceutical preparations (e.g., CYCLOSET® or PARLODEL®), providing a more stable, more efficient and more biologically compatible compound, with more predictable and reproducible effects, for pharmaceutical preparations of bromocriptine for the treatment of any of a variety of medical disorders including prediabetes, obesity, insulin resistance, hyperinsulinemia, hyperglycemia and type 2 diabetes mellitus (T2DM). The enhanced properties of pharmaceutical preparations of bromocriptine citrate cannot be mimicked by the mere addition of citrate to pharmaceutical preparations of bromocriptine mesylate. Due to its increased solubility in water, bromocriptine citrate displays increased absorption in vivo as compared to bromocriptine mesylate.

It is a further objective of the present invention to provide a more effective process, or method, for regulating, and improving metabolic disorders of vertebrates, i.e., animals, including humans.

In particular, it is a further object to provide a more effective process for resetting the circadian neural centers of animals, including humans, to produce long lasting changes in the amount of body fat stores, fatty liver, NASH, the sensitivity of the cellular response of a species to insulin, and overcome hyperinsulinemia and/or hyperglycemia which generally accompanies insulin resistance.

Another more specific object is to provide a more effective process for resetting the central (brain) circadian neural centers of animals, including humans, to treat metabolic disorders including T2DM or other endocrine or immune disorders or diseases on a long term basis.

These objects and others are achieved in accordance with the present invention by the administration of timed daily dosages to a vertebrate, animal or human, of the prolactin-inhibiting, ergot-related compound bromocriptine citrate, or 2-bromo-alpha-ergocryptine citrate. The dosages are continued on a daily basis for a period sufficient to treat metabolic disorders.

Bromocriptine citrate may be administered, with or without a dopamine $D_1$ receptor agonist such as SKF-38393, SKF-82958 or SKF-82957 to treat one or more of the metabolic disorders associated with MS, including, e.g., T2DM, hypertension, hypertriglyceridemia, a pro-inflammatory state, insulin resistance, fatty liver, NASH, CVD, and/or obesity-Bromocriptine citrate may further optionally be administered in conjunction with one or more of an alpha-1 adrenergic antagonist, an alpha-2 adrenergic agonist, or a serotonergic inhibitor, optionally further in combination with a serotonin $5HT_{1b}$ agonist. Examples of such agents are known in the art and are disclosed in, e.g., U.S. Pat. No. 5,877,183. Bromocriptine citrate may still further optionally be administered in conjunction with various peripheral acting agents, e.g., HMGCoA reductase inhibitors, anti-hypertensives, anti-diabetes agents including, e.g., postprandial insulin secretagogues or insulin itself, anti-inflammatory agents, and anti-coagulative agents. Examples of such agents are known in the art and are disclosed in, e.g., Int'l. Pat. App. Pub. No. WO 2009/091576 A2.

Bromocriptine citrate is administered to the vertebrate, animal or human, preferably orally or sublingually, optionally parenterally, for the treatment of any one or more symptoms desirable of change, e.g., obesity or hyperglycemia. (Pharmaceutical) dosage forms are solid or free-flowing. Dosage forms for sublingual or buccal administration include, but are not limited to, oral sprays, drops, solutions, colloidal suspensions, hard or soft capsules, coated or uncoated tablets, ointments, lozenges, films, chewing gums, chewable tablets, and/or liquid gargle. "Parenterally" is defined herein to mean administration and absorption of a substantial amount of bromocriptine citrate through other than the gastric and/or intestinal mucosa of the gastrointestinal tract. See, e.g., Int'l. Pat. App. Pub. No. WO 2009/091576 A2 for examples of parenteral formulations. Routes of parenteral administration include, without limitation, buccal, sublingual, subcutaneous, intravenous, nasal, otic, ocular, rectal, vaginal, or upper respiratory mucosa, or through the skin or lungs. Accordingly, dosage forms include, without limitation, injection, oral, otic, ophthalmic, or nasal sprays or drops, respiratory inhalers, sublingual and/or buccal sprays, drops, tablets, solutions, colloidal suspensions, and/or ointments, hard or soft capsules, coated or uncoated tablets, sachets, lozenges, films, chewing gum, chewable tablets, liquid gargle, skin patches, ointments, lotions, creams, aerosols, or rectal or vaginal suppositories.

Dosage forms for nasal administration include nasal sprays, drops, and ointments. Dosage forms for auricular or ocular administration include sprays, drops, ointments, lotions, and creams. Dosage forms for rectal administration include suppositories, sprays, drops, ointments, lotions, and creams. Dosage forms for vaginal administration include suppositories, sprays, drops, ointments, lotions, and creams. Dosage forms for upper respiratory mucosa or pulmonary administration include respiratory inhalers, e.g., nebulizers. Dosage forms for transdermal administration include skin patches, dermal sprays, drops, ointments, lotions, and creams.

Dosage forms may comprise one or more pharmaceutically acceptable excipients, including, e.g., one or more of a low moisture content filler such as anhydrous corn starch, a water-scavenging agent such as silicon dioxide, and/or a lubricant such as stearic acid. Non-limiting examples of pharmaceutically acceptable excipients useful in preparing bromocriptine citrate pharmaceutical formulations include, e.g., cornstarch, mannitol, colloidal silicon dioxide, and stearic acid. The pharmaceutically acceptable excipients may also include, e.g., one or more agents (e.g., a disintegrating agent such as for example Pharmaburst®, a release-controlling agent such as for example hydroxypropylmethyl cellulose, a, a cellular permeation enhancer such as for example sodium palmitate, a bioadhesive such as for example Kollidon, chitosan, cellulose derivatives, Carbopol 934P or 974P, carbolpole resins, polyvinyl alcohol, polyacrylic acid or polyvinyl pyrrolidone, and/or a stability enhancer such as citric acid, ascorbic acid, polyvinyl pyrrolidone, hyaluronic acid, sodium citrate, fatty acids, fatty alcohols and polyvinyl alcohols) that affect the rate of bromocriptine citrate release from the dosage form. Further examples of pharmaceutically acceptable excipients are known in the art and are disclosed in, e.g., Int'l. Pat. App. Pub. No. WO 2009/091576 A2.

The pharmaceutical compositions of the invention should include an amount of the compound(s) of the invention effective for treatment of metabolic diseases and disorders such as, but not limited to, T2DM, obesity, prediabetes, MS, cardiometabolic risk, hypertension, dyslipidemia, insulin resistance, hyperinsulinemia, hepatic steatosis, renal disease, cardiovascular disease, cerebrovascular disease, and peripheral vascular disease and biomarkers of impending vascular disease. The effective dosage will depend on the severity of the diseases and the activity of the particular compound(s) employed, and is thus within the ordinary skill of the art to determine for any particular host mammal or other host organism. Suitable dosages of bromocriptine citrate for a vertebrate (e.g., a human) may be, e.g., in the range of about 0.05 µg to about 0.5 mg per kg BW, optionally in the range of about 0.1 µg to about 0.3 mg per kg BW or in one preferred embodiment between about 2 µg and 0.1 mg/kg, BW per day. A suitable pharmaceutical dosage form comprising bromocriptine citrate may have a total weight of, e.g., (including excipients) of between about 2.5 mg and about 2000 mg.

The dosage forms disclosed herein are useful in treating medical disorders and diseases including metabolic disorders including type 2 diabetes mellitus (T2DM) by adjusting the circadian rhythm of central dopaminergic activity to mimic that of a healthy individual of the same species and sex. For example, in humans, such dosage forms are used in a manner preferably to increase central dopaminergic activity at about 4 hours within the time of waking in the morning, more preferably within about 2 hours of waking in the morning.

In the following Examples, experiments are described for comparing the aqueous solubility of bromocriptine citrate versus bromocriptine mesylate, and the rate of degradation of bromocriptine citrate versus bromocriptine mesylate at various temperatures and aqueous concentrations (including temperatures and concentrations within, respectively, the usual physiological and clinical treatment range).

All patents, patent applications, and literature references cited or discussed in this specification are hereby incorporated by reference in their entireties. In case of conflict, the present disclosure controls.

EXAMPLES

Example 1

Citric acid was dissolved, in separate reaction vessels, in one of either methanol, ethanol, or butanol at about 4 mg per ml at room temperature (solutions 1-3). Free base bromocriptine was dissolved in separate reaction vessels in either methanol, ethanol, or butanol at about 12 mg per 5-30 ml (solutions 4-6). The like organic solutions of citric acid and of bromocriptine (i.e., ethanol-ethanol, methanol-methanol, butanol-butanol) were then mixed in an equi-mole amount of bromocriptine and citrate. The three resulting solutions were stirred for about 2-24 hours on low heat (about 40 C) until the solvent evaporated to dryness. The resulting solid product in each reaction vessel contains bromocriptine citrate.

Example 2: Solubility of Bromocriptine Citrate Relative to Bromocriptine Mesylate Solid samples of equal amounts of bromocriptine mesylate and bromocriptine citrate added, under various pH conditions, to equal volumes of water or water/organic solutions in different vessels and the dissolution of the bromocriptine samples (aqueous solubility) was assessed over time. Bromocriptine citrate was found to dissolve much more quickly and with significantly greater solubility (increased mg of bromocriptine dissolved per ml of water in the citrate vs mesylate salt form) compared to bromocriptine mesylate.

Example 3: Stability of Bromocriptine Citrate Relative to Bromocriptine Mesylate Pharmaceutical preparations of bromocriptine mesylate and bromocriptine citrate are exposed to atmospheric conditions (40° C. and 70% relative humidity) and the degradation of the bromocriptine is assessed over time. The degradation of the bromocriptine from the citrate salt compound (bromocriptine citrate) is found to be substantially less than the degradation of the bromocriptine from the mesylate salt compound (bromocriptine mesylate) over a three-month period While the invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

What is claimed is:

1. A pharmaceutical dosage form comprising bromocriptine citrate wherein the bromocriptine citrate has greater water solubility and improved stability compared to bromocriptine mesylate.

2. The pharmaceutical dosage form of claim 1 further comprising a pharmaceutically acceptable excipient.

3. The pharmaceutical dosage form of claim 2 comprising an oral dosage form.

4. The pharmaceutical dosage form of claim 2 further comprising at least one excipient that affects the rate of bromocriptine citrate release from said dosage form.

5. The pharmaceutical dosage form of claim 2 further comprising a disintegrating agent.

6. The pharmaceutical dosage form of claim 2 comprising between about 0.05 µg and about 0.5 mg/kg of body weight of bromocriptine citrate.

7. The pharmaceutical dosage form of claim 2 wherein said dosage form has a total weight of between about 2.5 mg and about 2000 mg.

8. The pharmaceutical dosage form of claim 2 wherein said dosage form is a parenteral dosage form.

9. The pharmaceutical dosage form of claim 2 wherein the pharmaceutically acceptable excipient includes a disintegrating agent.

10. The pharmaceutical dosage form of claim 2 wherein said dosage form is a tablet.

11. The pharmaceutical dosage form of claim 2 wherein the disintegrating agent affects the rate of bromocriptine citrate release from the dosage form.

12. A parenteral dosage form comprising bromocriptine citrate and a pharmaceutically acceptable excipient.

13. The parenteral dosage form of claim 12 wherein the bromocriptine citrate comprises a tablet.

14. The parenteral dosage form of claim 12 wherein said dosage form has a total weight of between about 2.5 mg and about 2000 mg.

15. The parenteral dosage form of claim 12 further comprising at least one excipient that affects the rate of bromocriptine citrate release from said dosage form.

16. The parenteral dosage form of claim 12 wherein the bromocriptine citrate has greater water solubility and improved stability compared to bromocriptine mesylate.

17. A pharmaceutical dosage form comprising bromocriptine citrate.

18. The pharmaceutical dosage form of claim 17 further comprising a pharmaceutically acceptable excipient.

19. The pharmaceutical dosage form of claim 17 wherein the pharmaceutically acceptable excipient comprises at least one member selected from the group consisting of a bioadhesive, a disintegrating agent and a permeation enhancer.

20. The pharmaceutical dosage form of claim 17 comprising an oral dosage form.

21. The pharmaceutical dosage form of claim 18 further comprising at least one excipient that affects the rate of bromocriptine citrate release from said dosage form.

22. The pharmaceutical dosage form of claim 18 comprising between about 0.05 µg and about 0.5 mg/kg of body weight of bromocriptine citrate.

23. The pharmaceutical dosage form of claim 18 wherein the excipient comprises at least one of mannitol, citric acid, stearic acid, or colloidal silicon dioxide.

24. The pharmaceutical dosage form of claim 15 wherein said dosage form has a total weight of between about 2.5 mg and about 2000 mg.

25. The pharmaceutical dosage form of claim 18 wherein said dosage form is a parenteral dosage form.

26. The parenteral dosage form of claim 18 further comprising at least one excipient that affects the rate of bromocriptine citrate release from said dosage form.

27. A pharmaceutical dosage form comprising bromocriptine citrate wherein the bromocriptine citrate has greater water solubility compared to bromocriptine mesylate.

28. The pharmaceutical dosage form of claim 27 further comprising a pharmaceutically acceptable excipient.

29. The pharmaceutical dosage form of claim 27 comprising between about 0.05 µg and about 0.5 mg/kg of body weight of bromocriptine citrate.

30. The pharmaceutical dosage form of claim 29 comprising a parenteral dosage form.

31. The pharmaceutical dosage form of claim 2 comprising a sublingual dosage form.

* * * * *

UNITED STATES PATENT AND TRADEMARK OFFICE
CERTIFICATE OF CORRECTION

| | | |
|---|---|---|
| PATENT NO. | : 11,878,974 B2 | Page 1 of 2 |
| APPLICATION NO. | : 17/149017 | |
| DATED | : January 23, 2024 | |
| INVENTOR(S) | : Anthony H. Cincotta | |

It is certified that error appears in the above-identified patent and that said Letters Patent is hereby corrected as shown below:

On the Title Page

<u>In Other Publications:</u>
Column 2, Line 17 – delete "93735Pharmacological" and insert -- 93735 Pharmacological --.

In the Specification

Column 2, Line 66 – delete "inflammation)" and insert -- inflammation;) --.

Column 3, Line 47-48 – delete "erfotoxine," and insert -- ergotoxine, --.

Column 3, Line 49 – delete "IO" and insert -- 10 --.

Column 4, Line 2 – delete "secretagouges" and insert -- secretagogues --.

Column 5, Line 2 – delete "steatotic hepatitis" and insert -- steatohepatitis --.

Column 9, Line 10 – after "Method 5" insert -- : --.

Column 9, Line 25 – delete "point)." and insert -- point. --.

Column 9, Line 37 – delete "bromorcriptine" and insert -- bromocriptine --.

Column 11, Line 39-40 – delete "hydroxprophlmethyl cellulose," and insert -- hydroxpropyl methylcellulose, --.

Column 11, Line 40 – after "cellulose," delete "a,".

Column 11, Line 43 – delete "carbolpole" and insert -- carbopol --.

Signed and Sealed this
Fourth Day of June, 2024

Katherine Kelly Vidal
*Director of the United States Patent and Trademark Office*

CERTIFICATE OF CORRECTION (continued)
U.S. Pat. No. 11,878,974 B2

Column 13, Line 4 – after "period" insert -- . --.

In the Claims

Column 14, Line 27, Claim 24 – delete "claim 15" and insert -- claim 18 --.

Column 14, Line 32, Claim 26 – delete "parenteral dosage" and insert -- pharmaceutical dosage --.